(12) United States Patent
Benson

(10) Patent No.: US 6,284,466 B1
(45) Date of Patent: Sep. 4, 2001

(54) METHOD OF DETECTING GENETIC POLYMORPHISMS USING OVER REPRESENTED SEQUENCES

(75) Inventor: Andrew Benson, Lincoln, NE (US)

(73) Assignee: The Board of Regents of University of Nebraska, Lincoln, NE (US)

( * ) Notice: Subject to any disclaimer, the term of this patent is extended or adjusted under 35 U.S.C. 154(b) by 0 days.

(21) Appl. No.: 09/398,499

(22) Filed: Sep. 17, 1999

Related U.S. Application Data

(60) Provisional application No. 60/101,011, filed on Sep. 18, 1998.

(51) Int. Cl.⁷ ............... C12Q 1/68; C12P 19/34

(52) U.S. Cl. ............... 435/6; 435/91.2

(58) Field of Search ............... 435/6, 91.2, 810

(56) References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 5,126,239 | 6/1992 | Livak et al. | 435/6 |
| 5,589,579 | * 12/1996 | Torczynski et al. | 536/23.1 |
| 5,695,940 | 12/1997 | Drmanac et al. | 435/6 |
| 5,753,467 | 5/1998 | Jensen et al. | 435/91.2 |
| 5,874,215 | 2/1999 | Kuiper et al. | 435/6 |
| 6,110,667 | * 8/2000 | Lopez-Nieto et al. | 435/6 |

FOREIGN PATENT DOCUMENTS

| | | | |
|---|---|---|---|
| 804618B1 | 11/1997 | (EP) | C12Q/1/68 |
| WO 93/08297 | 4/1993 | (WO) | |
| WO 93/22454 | 11/1993 | (WO) | |
| 95/31574 | * 11/1995 | (WO) | |
| WO 97/22720 | 6/1997 | (WO) | |

OTHER PUBLICATIONS

Griffais et al., Nucleic Acids Res. 19(14), 3887–3891, 1991.*

Botstein, et al, *Construction of a Genetic Linkage Map in Man Using Restriction Fragment Length Polymorphisms*, Am, J. Hum. Genet., 1980, vol. 342, p. 314.

Ochman and Selander, *Standard Reference of Escherichia coli from Natural Propulations*, Journal of Bacteriology, 1984, vol. 157, pp. 690–693.

Saitou et al., *The Neighbor–joining Method: A New Method for Reconstructing Phylogenetic Trees*, Mol. Biol. Evol., 1987, vol. 4, pp. 406–425.

Williams, et al., *DNA polymorphisms amplified by arbitrary primers are useful as genetic markers*, Nucleic Acid Research., 1990, vol. 18, p. 6531–6535.

Guan et al., *Rapid Generation of Whole Chromosome Painting Probes (WCPs) by Chromosome Microdissection*, Genomics, 1994, vol. 22, pp. 101–107.

(List continued on next page.)

*Primary Examiner*—Kenneth R. Horlick
(74) *Attorney, Agent, or Firm*—Senniger, Powers, Leavitt & Roedel

(57) ABSTRACT

A method is disclosed for the detection of polymorphisms in a DNA sequence based on nucleotide differences. DNA sequences from different sources are amplified by the polymerase chain reaction using primers based on strand biased, over represented oligonucleotide sequences and differences in the nucleotide sequences of the amplification products determined. Also disclosed are methods for the identification of individuals, or the species, strain or serotype of an organism using the method of the present invention. In addition, kits are disclosed for the determination of polymorphisms using the method of the present invention. The ability to determine genetic polymorphisms has widespread application in areas such as genome mapping, genetic linkage studies, medical diagnosis, epidemiological studies, forensics and agriculture.

51 Claims, 3 Drawing Sheets

OTHER PUBLICATIONS

Lee, et al., *Genomic analysis using pulsed–field gel electrophoresis of Escherichia coli 0157: H7 isolated from dairy calves during the United States national dairy heifer evaluation project* (1991–1992) Veterinary Microbiology, 1996, vol. 48, pp. 223–230.

Blattner, et al., *The Complete Genome Sequence of Escherichia coli K–12*, Science, 1997, vol. 277, pp. 1453–1462.

Shere, et al., *Longitudinal Study of Escherichia coli 0157: H7 Dissemination of Four Dairy Farms in Wisconsin*, Applied Environ. Microbiol., 1998, vol. 64, pp. 1390–1399.

Gouveia et al., *Genomic Comparisons and Shiga Toxin Production amon Escherichia coli 0157: H7 Isolates from a Day Care Center Outbreak and Sporadic Cases in Southeastern Wisconsin*, Journal of Clin. Microbiol., 1998, vol. 36, pp. 727–733.

Salzberg et al., *Skewed oligomers and origins of replication*, Gene, 1998, vol. 217, pp. 57–67.

Boerlin et al., *Evolution of Enterohemorrhagic Escherichia coli Hemolysin Plasmids and the Locus for Enterocyte Effacement in Shiga Toxin–Producing E. coli*, Infect. Immun., 1998, vol. 66, pp. 2553–2561.

Christian et al., *PCR in situ followed by microdissection allows whole chromosome painting probes to be made from single microdissected chromosomes*, Mammalian Genome, 1999, vol. 10, pp. 628–631.

\* cited by examiner

SEQUENCE LISTING

<160> NUMBER OF SEQ ID NOS: 58

<210> SEQ ID NO 1
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 1 cgctggcg                                                                8

<210> SEQ ID NO 2
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 2 ggcgctgg                                                                8

<210> SEQ ID NO 3
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 3 gctggtgg                                                                8

<210> SEQ ID NO 4
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 4 gctggcgg                                                                8

<210> SEQ ID NO 5
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 5 tgctggcg                                                                8

<210> SEQ ID NO 6
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 6 gcgctggc                                                                8

<210> SEQ ID NO 7
<211> LENGTH: 8

```
<212> TYPE: DNA
<213> ORGANISM: Artificial Sequence
<220> FEATURE:
<223> OTHER INFORMATION: Description of Artificial Sequence:Primer

<400> SEQUENCE: 7 tggcgctg                                                                    8

<210> SEQ ID NO 8
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 8 gctggcgc                                                                    8

<210> SEQ ID NO 9
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 9 cgctggtg                                                                    8

<210> SEQ ID NO 10
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 10 ctggcggc                                                                    8

<210> SEQ ID NO 11
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 11 ctggcgca                                                                    8

<210> SEQ ID NO 12
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 12 gctggcga                                                                    8

<210> SEQ ID NO 13
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 13
``` tggcggcg                                                            8

<210> SEQ ID NO 14
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 14 aactggcg                                                            8

<210> SEQ ID NO 15
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 15 gctggaag                                                            8

<210> SEQ ID NO 16
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 16 ctggcgcg                                                            8

<210> SEQ ID NO 17
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 17 gcgctgga                                                            8

<210> SEQ ID NO 18
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 18 ctggcgaa                                                            8

<210> SEQ ID NO 19
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 19 tgctggtg                                                            8

<210> SEQ ID NO 20
<211> LENGTH: 8
<212> TYPE: DNA
<213> ORGANISM: Artificial Sequence

```
<220> FEATURE:
<223> OTHER INFORMATION: Description of Artificial Sequence:Primer

<400> SEQUENCE: 20 ctggtggt                                                              8

<210> SEQ ID NO 21
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 21 ctggtggc                                                              8

<210> SEQ ID NO 22
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 22 cggtggcg                                                              8

<210> SEQ ID NO 23
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 23 tgcgctgg                                                              8

<210> SEQ ID NO 24
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 24 cgccagcg                                                              8

<210> SEQ ID NO 25
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 25 ccagcgcc                                                              8

<210> SEQ ID NO 26
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 26 ccaccagc                                                              8
```

```
<210> SEQ ID NO 27
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 27 ccgccagc                                                                 8

<210> SEQ ID NO 28
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 28 cgccagca                                                                 8

<210> SEQ ID NO 29
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 29 gccagcgc                                                                 8

<210> SEQ ID NO 30
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 30 cagcgcca                                                                 8

<210> SEQ ID NO 31
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 31 gcgccagc                                                                 8

<210> SEQ ID NO 32
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 32 caccagcg                                                                 8

<210> SEQ ID NO 33
<211> LENGTH: 8
<212> TYPE: DNA
<213> ORGANISM: Artificial Sequence
<220> FEATURE:
<223> OTHER INFORMATION: Description of Artificial Sequence:Primer
```

```
<400> SEQUENCE: 33 gccgccag                                                                    8

<210> SEQ ID NO 34
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 34 tgcgccag                                                                    8

<210> SEQ ID NO 35
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 35 tcgccagc                                                                    8

<210> SEQ ID NO 36
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 36 cgccgcca                                                                    8

<210> SEQ ID NO 37
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 37 cgccagtt                                                                    8

<210> SEQ ID NO 38
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 38 cttccagc                                                                    8

<210> SEQ ID NO 39
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 39 cgcgccag                                                                    8

<210> SEQ ID NO 40
```

```
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 40 tccagcgc                                                              8

<210> SEQ ID NO 41
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 41 ttcgccag                                                              8

<210> SEQ ID NO 42
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 42 caccagca                                                              8

<210> SEQ ID NO 43
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 43 accaccag                                                              8

<210> SEQ ID NO 44
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 44 gccaccag                                                              8

<210> SEQ ID NO 45
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 45 cgccaccg                                                              8

<210> SEQ ID NO 46
<211> LENGTH: 8
<212> TYPE: DNA
<213> ORGANISM: Artificial Sequence
<220> FEATURE:
<223> OTHER INFORMATION: Description of Artificial Sequence:Primer

<400> SEQUENCE: 46
``` ccagcgca                                                      8

<210> SEQ ID NO 47
<211> LENGTH: 10
<212> TYPE: DNA
<213> ORGANISM: Artificial Sequence
<220> FEATURE:
<223> OTHER INFORMATION: Description of Artificial Sequence:Primer

<400> SEQUENCE: 47
atgctggtgg                                                    10

<210> SEQ ID NO 48
<211> LENGTH: 10
<212> TYPE: DNA
<213> ORGANISM: Artificial Sequence
<220> FEATURE:
<223> OTHER INFORMATION: Description of Artificial Sequence:Primer

<400> SEQUENCE: 48
atgctggcgg                                                    10

<210> SEQ ID NO 49
<211> LENGTH: 10
<212> TYPE: DNA
<213> ORGANISM: Artificial Sequence
<220> FEATURE:
<223> OTHER INFORMATION: Description of Artificial Sequence:Primer

<400> SEQUENCE: 49
attggcgctg                                                    10

<210> SEQ ID NO 50
<211> LENGTH: 10
<212> TYPE: DNA
<213> ORGANISM: Artificial Sequence
<220> FEATURE:
<223> OTHER INFORMATION: Description of Artificial Sequence:Primer

<400> SEQUENCE: 50
atgctggcga                                                    10

<210> SEQ ID NO 51
<211> LENGTH: 10
<212> TYPE: DNA
<213> ORGANISM: Artificial Sequence
<220> FEATURE:
<223> OTHER INFORMATION: Description of Artificial Sequence:Primer

<400> SEQUENCE: 51
atgcgctgga                                                    10

<210> SEQ ID NO 52
<211> LENGTH: 10
<212> TYPE: DNA
<213> ORGANISM: Artificial Sequence
<220> FEATURE:
<223> OTHER INFORMATION: Description of Artificial Sequence:Primer

<400> SEQUENCE: 52
atctggcgaa                                                    10

<210> SEQ ID NO 53
<211> LENGTH: 10
<212> TYPE: DNA

```
<213> ORGANISM: Artificial Sequence
<220> FEATURE:
<223> OTHER INFORMATION: Description of Artificial Sequence:Primer

<400> SEQUENCE: 53
atcgccagcg                                                            10

<210> SEQ ID NO 54
<211> LENGTH: 10
<212> TYPE: DNA
<213> ORGANISM: Artificial Sequence
<220> FEATURE:
<223> OTHER INFORMATION: Description of Artificial Sequence:Primer

<400> SEQUENCE: 54
atccgccagc                                                            10

<210> SEQ ID NO 55
<211> LENGTH: 10
<212> TYPE: DNA
<213> ORGANISM: Artificial Sequence
<220> FEATURE:
<223> OTHER INFORMATION: Description of Artificial Sequence:Primer

<400> SEQUENCE: 55
atgccagcgc                                                            10

<210> SEQ ID NO 56
<211> LENGTH: 10
<212> TYPE: DNA
<213> ORGANISM: Artificial Sequence
<220> FEATURE:
<223> OTHER INFORMATION: Description of Artificial Sequence:Primer

<400> SEQUENCE: 56
atgcgccagc                                                            10

<210> SEQ ID NO 57
<211> LENGTH: 10
<212> TYPE: DNA
<213> ORGANISM: Artificial Sequence
<220> FEATURE:
<223> OTHER INFORMATION: Description of Artificial Sequence:Primer

<400> SEQUENCE: 57
attgcgccag                                                            10

<210> SEQ ID NO 58
<211> LENGTH: 10
<212> TYPE: DNA
<213> ORGANISM: Artificial Sequence
<220> FEATURE:
<223> OTHER INFORMATION: Description of Artificial Sequence:Primer

<400> SEQUENCE: 58
atcttccagc                                                            10
```

METHOD OF DETECTING GENETIC POLYMORPHISMS USING OVER REPRESENTED SEQUENCES

CROSS-REFERENCE TO RELATED APPLICATIONS

This application claims priority to U.S. provisional application Ser. No. 60/101,011, filed Sep. 18, 1998, and hereby incorporated by reference.

FIELD OF THE INVENTION

This invention relates to a method for the determination of polymorphisms present in DNA sequences by amplification using primers based on strand biased, over-represented oligonucleotide sequences.

BACKGROUND OF THE INVENTION

Nucleic acid polymorphism provides a means to identify species, serotypes, strains, varieties, breeds or individuals based on differences in their genetic make up. Nucleic acid polymorphism can be caused by nucleotide substitution, insertion or deletion. The ability to determine genetic polymorphism has widespread application in areas such genome mapping, genetic linkage studies, medical diagnosis, epidemiological studies, forensics and agriculture. Several methods have been developed to compare homogenous segments of DNA to determine if polymorphism exists. All of these methods, however, suffer from several shortcomings which limit their practical application.

The most direct method for detection of polymorphism is by direct comparison of sequences of different genomes. Although the development of automated sequencing methods has greatly lessened the time and effort required to sequence DNA, the size of the genome for even simple prokaryotic organisms is so large that direct sequence is impractical for routine detection of polymorphisms.

One method for determination of genetic polymorphism in genomic DNA is by pulsed field gel electrophoresis. Pulse field gel electrophoresis or PFGE is used to detect differences in large fragments of genomic DNA. In PFGE, pulsed, alternating, orthogonal electric fields are applied to the gel. Large molecules of DNA migrating through the gel become trapped in their reptation tubes each time the direction of the electric field is altered. The progress for the DNA through the gel is then halted until the DNA has had sufficient time to reorient itself along the new axis of the electric field. The degree of resolution of PFGE depends on several factors including the uniformity of the electric fields, the absolute lengths of the electric pulses, the ratio of the pulse lengths used to generate the electric fields, the angles of the two electric fields to the gel, and the relative strengths of the electric fields. Several variations of PFGE have been developed to increase the resolution, however, the technique remains useful only for the detection of relatively large differences, generally 5–10 kb, between DNA molecules Another method for the detection of genetic differences is restriction fragment length polymorphism or RFLP (Botstein et al. *Am. J. Hum. Genet.* 342:314, 1980). RFLP is based on the specificity with which restriction enzymes cleave DNA. A restriction enzyme will cleave DNA only when a particular sequence is present. Any alteration in the sequence will result in the enzyme being unable to cleave the DNA at that site, which in turn results in a change in the size of the fragment produced. Changes elsewhere in the sequence may introduce new recognition sites within the sequence, again altering the size distribution of the restriction fragments. Changes in the DNA sequence caused by insertions, deletions and inversions will also result in changes in the size of the fragments produced and so can also be detected by RFLP. Essentially any restriction enzyme can be used in RFLP and combinations of enzymes can also be used.

Differences in the size of restriction enzyme fragments are typically determined by Southern blots (Southern, *J. Mol. Biol.* 98:103, 1975). After digestion by the restriction enzyme of choice, the resulting fragments are size separated by gel electrophoresis, transferred to a membrane, and hybridized with labeled probe corresponding to a particular area of the genome. RFLP has proved to be a powerful tool in genetic analysis, but often requires a great deal of optimization in order to obtain low background to signal ratios to allow detection of polymorphic markers. Also the method is limited to sequences that can be detected by the DNA probes used. In addition, point mutations can usually be detected only if they occur in a restriction site.

Another method for determining genetic polymorphism uses primers of an arbitrary sequence to amplify DNA by the polymerase chain reaction (PCR) (Williams et al., *Nuc. Acid Res.* 18:6531, 1990; U.S. Pat. No. 5,126,239). Because the primers are not designed to amplify a specific sequence, the technique is called randomly amplified polymorphic DNA or RAPD. The primers used are at least seven nucleotides in length and typically are between nine to thirteen bases with a G+C content of between 50–80% and no palindromic sequences. Under the proper conditions, differences as small as a single nucleotide can affect the binding of the primer to the template DNA, thus resulting in differences in the distribution of amplification products produced between genomes. The RAPD method of identifying polymorphisms is faster and more readily adaptable to automation than is RFLP. A limitation on the use of RAPD is the random nature of the primers used, so that maximal coverage of the genome is not assured. To the contrary, the random nature of the amplification, raises that possibility that large portions of the genome will not be amplified so that useful areas of polymorphism may go undetected.

Yet another method for identifying and mapping genetic polymorphisms has been termed amplified fragment length polymorphism or AFLP (U.S. Pat. No. 5,874,215). AFLP combines the use of restriction enzymes as in RFLP with the use of PCR as in RAPD. Briefly, restriction fragments are produced by the digestion of genomic DNA with a single or a pair of restriction enzymes. If a pair of enzymes is used, enzymes are paired based on differences in the frequency of restriction sites in the genome, such that one of the restriction enzymes is a "frequent cutter" while the remaining enzyme is a "rare cutter." The use of two enzymes results in the production of single and double digestion fragments.

Next, double stranded synthetic oligonucleotide adaptors of 10–30 bases are ligated onto the fragments generated. Primers are then designed based on the sequence of the adapters and the restriction site. When pairs of restriction enzymes are used, nucleotides extending into the restriction sites are added to the 3' end of the primers such that only fragments generated due to the action of both enzymes (double cut fragments) are amplified. Using this method, any polymorphism present at or near the restriction site will affect the binding of the primer and thus the distribution of the amplification products. In addition, any differences in the nucleotide sequence in the area flanked by the primers will also be detected. AFLP allows for the simultaneous co-amplification of multiple fragments. AFLP, however, is a multiple step process and detection of polymorphism, however, is limited to areas at or between restriction sites.

Another method to detect polymorphism is based on the high degree of length variation of certain tandemly repeating nucleotide sequences in most, if not all, eukaryotes variously called simple sequence repeats (SSR), simple sequence length polymorphisms (SSLP), dinucleotide, trinucleotide, tetranucleotide, or pentanucleotide repeats, and microsatellites. Various workers have shown that microsatellites can be useful in detecting polymorphisms (See, Morgante et al. EP 0804618 B1 and references cited therein). In this method, primers are designed based on the sequence of the microsatellite sequences. In one variation, the primers contain 2 to 4 additional nucleotides that flank the microsatellite sequence in order to anchor the primers to a particular site at each microsatellite locus. Although microsatellite-directed primers are highly effective at detecting polymorphism, they cannot be used in prokaryotes which lack microsatellite DNA.

Jensen et al., U.S. Pat. No. 5,753,467, discloses a method for the identification of microorganisms by amplification of variable regions within ribosomal DNA sequences. Briefly, primers are used the bind to highly conserved regions that flank variable regions within rDNA sequences. Size differences in the amplification products generated are then used to identify the microorganism. Although useful for identification purposes, the method provides no information about the rest of the genome and so is of limited use in genome mapping and genetic linkage studies.

Recently, the elucidation of the complete genome sequence of *Escherichia coli* K-12, (Blattner et al., *Science* 277:1453, 1997) has revealed the presence of a series of over represented (500–900 occurrences) oligonucleotide sequences within the genome. By over represented it is meant that the oligonucleotide sequences are present at a greater frequency that would be expected statistically. These oligonucleotides have been found to be biased (skewed) to the leading strand of DNA. The most frequent oligonucleotides in the leading strand consist of octamers, most containing the trimer CTG, often within the pentamer GCTGG. Although there is no direct proof, the complements of these oligonucleotides have been suggested to serve as priming sites for DNA replication based on their spacing and the presence of the possible DnaG primase binding site CAG.

The Applicant has used these over represented oligonucleotide sequences to invent a novel method to detect polymorphisms in the genome of an organism. The method makes use of these over represented oligonuclotides as priming sites for amplification of DNA by the polymerase chain reaction. The method of the present invention has several advantages over the prior art. The areas amplified are spread throughout the entire genome, thus detection of polymorphism is not restricted to a limited area. Surprisingly, it has been found that a single reaction can result in coverage of approximately 5% of the total *E. coil* genome. Thus, it is possible to cover the entire genome of an organism such as *E. coli* with as few as 20 primer pairs. The primers used are rationally designed based on the over represented oligomers, thus limiting non-specific amplification. In addition, the method does not require the use of restriction enzymes or adaptors making it technically less cumbersome.

SUMMARY OF THE INVENTION

Accordingly, one aspect of the present invention provides a method for determining polymorphism in a DNA sequence based on nucleotide differences comprising amplifying a DNA sequence of interest by the polymerase chain reaction to produce amplification products using at least one pair of oligonucleotide primers. The DNA used can be directly obtained from cells or organisms or be cDNA produced by the reverse transcription of RNA. The first primer of the pair is based on an over represented oligonucleotide sequence biased to one strand of the DNA, while the second primer is based on a second over represented oligonucleotide sequence biased to the DNA strand complementary to the first strand. In a second reaction, the previous amplification is repeated for at least one additional DNA sequence from another source. The resulting amplification products are then analyzed by any method capable of detecting differences in nucleic acid sequences, for example, electrophoresis, hybridization (including the use of micro arrays), and sequencing. The results obtained for each DNA sequence are then compared.

In another aspect of the invention, a method is provided for the identification by species, serotype, or strain of an organism comprising obtaining DNA from the organism where the DNA contains over represented oligonucleotide sequences. The DNA used can be directly obtained from the organism or be cDNA produced by the reverse transcription of RNA. The DNA is amplified to produce amplification products using at least one pair of oligonucleotide primers. Each primer pair comprises a first primer based on an over represented oligonucleotide sequence biased to a first strand of DNA and a second primer based on a second over represented oligonucleotide sequence biased to a second strand of DNA which is complementary to the first strand. The amplification products are then analyzed by any method capable of detecting differences in nucleic acid sequences, for example, electrophoresis, hybridization (including micro arrays), and sequencing. The results obtained are then analyzed for amplification products in common with all members of a species and for products unique to strains or serotypes within a species. The results are then compared to a database of previously analyzed products allowing identification of the species, serotype or strain of the organism.

Another aspect of the invention provides a method for the identification of individuals comprising obtaining DNA from an individual whose DNA contains over represented sequences. The DNA used can be directly obtained from the individual or it can be cDNA produced by reverse transcription of RNA. The DNA is amplified to produce amplification products using at least one pair of oligonucleotide primers. Each primer pair comprises a first primer based on an over represented oligonucleotide sequence biased to a first strand of DNA and a second primer based on a second over represented oligonucleotide sequence biased to a second strand of DNA which is complementary to the first strand. The amplification products are then analyzed by any method capable of detecting differences in nucleic acid sequences, for example, electrophoresis, hybridization (including micro arrays), and sequencing. The results obtained are then compared to a database of previously amplified products. If the pattern obtained, matches a pattern in the database, then the individual can be identified. Conversely, if the pattern obtained does not match any pattern in the database, then individuals in the database can be excluded.

Yet another aspect of the invention provides a kit whose components can be used to practice the present invention. The kit comprises at least one pair of oligonucleotide primers, where each pair of primers comprises a first primer based on a first over represented oligonucleotide sequence biased to one strand of DNA and a second primer based on a second over represented oligonucleotide sequence biased to a strand of DNA complementary to the strand upon which the first primer is based. The kit further comprises a reaction solution comprising a buffer and a magnesium salt and instructions for using the kit to produce and detect amplification products from a nucleic acid sequence which can then be used to determine polymorphism or for identification of an organism.

Still another aspect of the invention provides a method for the determination of polymorphism on the basis of binding oligonucleotides to chromosomes. In this method, an oligonucletide containing a reporter moiety is produced containing an over represented oligonucleotide sequence. If desired, additional reporter containing oligonucleotides can be produced containing additional over represented oligonucleotide sequences. The oligonucleotides are then contacted with chromosomes from an organism and allowed to hybridize. This step is repeated with chromosomes from at least one additional organism. The locations of the oligonucleotides on the different sets of chromosomes are then detected and compared to determine differences in location of the oligonucleotides due to polymorphism. In addition to determining polymorphism, individuals or the species, serotype or strain of an organism can be identified based on the location of oligonucleotides bound to the chromosomes by comparing the results obtained to a database of previously obtained results as described previously.

BRIEF DESCRIPTION OF THE DRAWINGS

These and other features, aspects, and advantages of the present invention will become better understood with regard to the following description, appended claims, and accompanying drawings where:

DETAILED DESCRIPTION OF SPECIFIC EMBODIMENTS

Figure 1:
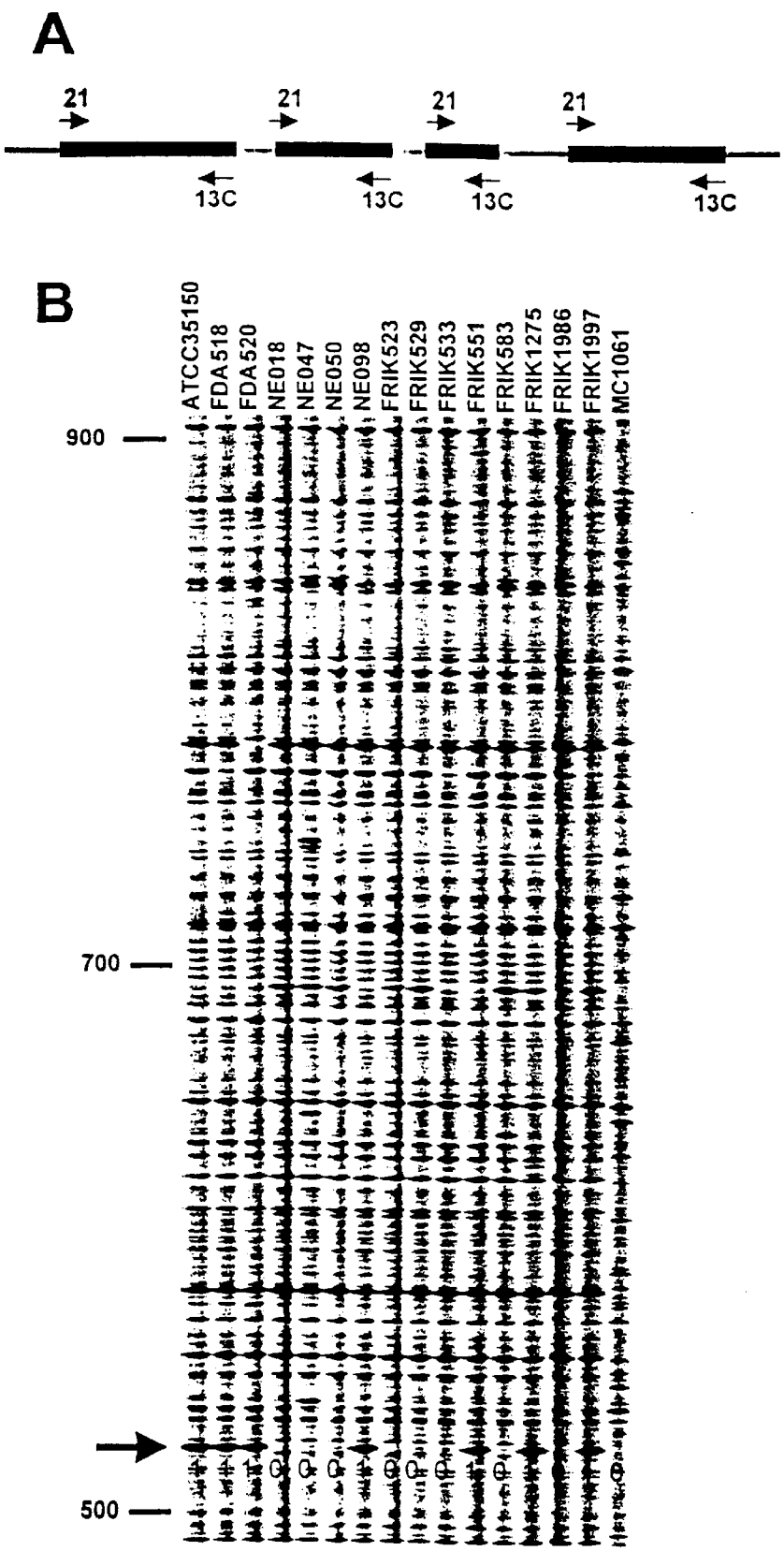
FIG. 1A shows the occurrence of a set of leading strand biased (Seq. No. 51) and lagging strand biased (Seq. No. 57) octamers, indicated by the arrows on a contiguous segment of a chromosome. The black rectangle between the arrows illustrates the segments of the genome that would be amplified by the method of the present invention with the primer pair based on the two octamers at primer saturation.
FIG. 1B shows a section of an image file for amplification products produced by the method of the present invention from E. coli O157:H7 strains ATCC 35150, FDA 518, FDA 520, NE 018, NE 047, NE 050, NE 098, FRIK 523, FRIK 529, FRIK 533, FRIK 551, FRIK 583, FRIK 1275, FRIK 1986, FRIK 1997, and the K-12 strain MC 1061 after data collection. Molecular sizes are indicated in base length on the left. The image was compacted approximately 10× vertically. The large arrow indicates an intense amplification product and the binary character scores for this band from each strain is indicated immediately below the band (1=presence, 0=absence).

All publications, patents, patent applications or other references cited in this application are herein incorporated by reference in their entirety as if each individual publication, patent, patent application or reference were specifically and individually indicated to be incorporated by reference.

As used herein, the term "oligonucleotide" means a molecule consisting of at least two deoxyribonucleotides or ribonucleotides joined by phosphodiester bonds.

As used herein the term "primer" or "oligonucleotide primer" means an oligonucleotide, either naturally occurring as in a purified restriction enzyme digest or produced synthetically, that under the proper conditions, is capable of binding to a template DNA or RNA molecule to initiate primer extension by polymerization, such as by DNA polymerase, to produce a DNA or RNA molecule that is complementary to the template molecule. It is preferred that primers be more than 5 but less than 30 nucleotides in length and do not contain palindromic sequences or sequences resulting in the formation of primer dimers. Preferably primers are single stranded, however, double stranded primers may be used provided the primer is treated to separate the strands prior to being used initiate primer extension.

As used herein "primer pair" means two primers that bind to opposite strands of a template nucleic acid molecule. The portion of the template nucleic acid molecule that is flanked by the primers is the target sequence.

As used herein the terms "target sequence" or "target DNA" or "target RNA" or "target nucleic acid sequence" mean nucleic acid sequences targeted for amplification or replication and subsequent analysis by the method of the present invention for detection of polymorphisms.

As used herein, the terms "DNA amplification", "nucleic acid amplification", "polynucleotide amplification", "nucleic acid amplification", or "primer extension" mean any method known in the art that results in the linear or exponential replication of nucleic acid molecules that are copies of a target nucleic acid sequence.

As used herein, the term "amplification products" means the copies of a target nucleic acid sequence(s) produced by nucleic acid amplification.

As used herein, the terms "complementary" "complementary DNA sequences", "complimentary nucleic acid sequences" or "complementary polynucleotide sequences" mean nucleic acid base sequences that can form a double-stranded structure by the formation of hydrogen bonds between matching base pairs.

As used herein, the term "reporter", "reporter molecule" or "reporter moiety" means any moiety capable of being detected by enzymatic means, immunological means, or energy emission, including, but not limited to, fluorescent molecules, radioactive tags, light emitting moieties, immunoreactive ligands, or affinity reactive ligands.

As used herein the terms "labeled oligonucleotide", "labeled primer", "labeled sequence", or "labeled nucleotide", "labeled polynucleotide", "labeled DNA", or "labeled RNA" refers to a nucleotide or nucleic acid sequence comprising a reporter moiety.

As used herein the term "over represented oligonucleotide sequence" means an oligonucleotide sequence whose occurrence is at least 5 times greater than would be predicted statistically by the method described herein and whose percentage skew as calculated by the method described herein is greater than 6.

As used herein, the term "radiometry" means the measurement of radiation by photography, as in exposure of x-ray film, by geiger-mueller tube, or by scintillation counting.

As used herein, the term "organism" means any living thing and includes human beings.

As used herein, the term "individual" means a single organism.

As used herein, the terms "hybridize" or "hybridization" refers to the formation of double stranded segments by polynucleotide or oligonucleotide strands through hydrogen bonding between complementary base pairs. The greater the extent of complementarity between the strands, the greater is the extent of formation of double stranded segments. The polynucleotide or oligonucleotide strands may be those of single stranded nucleic acids or they may be derived from denatured double stranded nucleic acids. The double stranded segments formed can be DNA/DNA, RNA/RNA or DNA/RNA.

The present invention provides a method for the detection of polymorphism in DNA sequences. The method can be used in any organism possessing over represented oligonucleotide sequences. The method involves amplification of DNA sequences by the polymerase chain reaction using primer pairs based on over represented oligonucleotide sequences. One primer of the pair is based on an over represented oligonucleotide sequence that is biased to a first DNA strand. The second primer is based on a second over represented oligonucleotide sequence that is biased to a second DNA strand that is complementary to the first strand. The amplification products obtained are then analyzed by any method that allows detection of polymorphism in nucleic acid sequences. The results of the analysis can then be used to identify an individual or the species, serotype, or strain of the organism from which the DNA was obtained. The results of the analysis can also be used in genetic studies such as the construction of linkage maps and determination of mutations resulting in changes in pathogenicity or environmental fitness.

The DNA used in the method of the present invention can be obtained from any source. DNA used in this method can be in either purified or non-purified form. In one embodiment, genomic DNA is isolated from bacteria, however, DNA obtained from any prokaryotic or eukaryotic organism can be used in the present invention. Methods for the isolation of DNA from microorganisms and cells are well known in the art (See, for example, Ausubel et al., *Short Protocols in Molecular Biology*, 2nd ed., Greene Publishing, 1992; Sambrook et al., *Molecular Cloning*, 2nd ed., Cold Spring Harbor Laboratory Press, 1989; Davis et al., *Basic Methods in Molecular Biology*, Elsevier, 1986). For example, bacterial genomic DNA can be isolated by phenol/chloroform extraction or by cesium chloride centrifugation.

Although in one preferred embodiment, double stranded DNA (dsDNA) is used to start the amplification process, the method of the present invention is not limited to dsDNA as a starting material. For example, RNA can be isolated from cells or organisms and converted into cDNA by reverse transcription. Methods for the isolation of RNA and reverse transcription are well known and can be found in standard laboratory texts such as Ausubel et al., *Short Protocols in Molecular Biology*, 2nd ed., Greene Publishing, 1992; Sambrook et al., *Molecular Cloning*, 2nd ed., Cold Spring Harbor Laboratory Press, 1989; Davis et al., *Basic Methods in Molecular Biology*, Elsevier, 1986. When single stranded DNA (ssDNA), for example cDNA, is used as the starting material, the procedure used is the same as with dsDNA except that during the first amplification cycle, only one primer will anneal and primer extension will result in the formation of a dsDNA molecule. In the next cycle, both primers of the primer pair will anneal, one to the original DNA molecule and the second to the newly synthesized DNA molecule.

Amplification is carried out using the polymerase chain reaction (PCR). Procedures for amplifying nucleic acid sequences using PCR have been previously described, for example, in Mullis et al., U.S. Pat. No. 4,683,195; Mullis, U.S. Pat. No. 4,683,202; and Innis et al., *PCR Protocols*, Academic Press, 1990.

The choice of nucleic acid polymerase used in the PCR reaction will vary with the starting template. For DNA templates, suitable DNA polymerases are available from a number of commercial sources. In one embodiment, a thermal stable DNA polymerase such as the polymerase obtained from the thermophillic bacterium *Thermus aquaticus* (Taq polymerase) is used. In another embodiment a variant of Taq polymerase, for example, SequiTherm™ (Epicentre, Madison, Wis.) is used. When RNA is used as the starting template, reverse transcriptase is an example of a polymerase that would be useful for the initial extension. Methods for amplification of RNA by reverse transcription followed by PCR (RT-PCR) are well known in the art and have been previously described in, for example, Innis et al., *PCR Protocols*, Academic Press, 1990 and Ausubel et al., *Short Protocol in Molecular Biology*, 2nd ed., John Wiley & Sons, 1992.

Primers used in the amplification reaction are based on over represented oligonucleotides within the genome of the species of interest. An oligonucleotide is over represented if it occurs at least 5 times more frequently than would be predicted statistically. As the frequency of the oligonucleotide sequence increase it is expected that the number of amplification products produced will also increase. Accordingly, oligonucleotide sequences whose occurrence is at least 6 times, at least 7 times, or at least 8 times greater than predicted can also be used. Thus, an oligonucleotide occurs at a frequency 7 times greater than predicted if its occurrence, $R > 7N/A^S$, where N is the length of the nucleic acid sequence, A is the alphabet size (for DNA A=4), and S is the length of the oligonucleotide. If the nucleic acid sequence comprises the entire genome of an organism, then N is the length of the genome. Therefore, for an organism such as *E. coli* K-12 with a genome of 4,639,221 bp, an octamer occurs 7 times greater than predicted when its occurrence exceeds $(7)(4,639,221)/4^8$ or 495. In some instances, it may be possible to practice the present invention using a primer based on an oligonucleotide whose occurrence does not exceed 5 times greater than predicted by pairing it with a primer based on an oligonucleotide whose occurrence is at least 8.5 times greater than expected.

In addition, over represented oligonucleotides must have a percent skew greater than 6 and preferably greater than 8 as calculated by the formula:

Percent skew=100×(f−f')/(f+f')

where f is the frequency of the oligonucleotide on the leading strand and f' is the frequency of the reverse complement of the same oligonucleotide on the leading strand (Blattner et al., *Science* 277:1453–1462, 1997).

The size of the oligonucleotide sequences chosen is not critically important. It will be apparent to those skilled in the art that as the size of the oligonucleotide increases its frequency within the nucleotide sequence to be examined will likely decrease. In one embodiment, the oligonucleotide sequences are from 6 to 30 nucleotides in length, in another embodiment, the oligonucleotide sequences are 6 to 15 nucleotides in length and in yet another embodiment, the oligonucleotide sequences are 8 nucleotides in length.

When selecting oligonucleotide sequences for primer design, it is preferred that the sequences chosen be widely distributed throughout the genome or nucleotide sequence to be examined. Alternatively, if a particular area of the genome is of interest, sequences that are widely represented within that area can be used. In one embodiment, the sequences used contain the internal sequence CAG. The CAG sequence is thought to serve as the site for initiation of primer synthesis by the DNA primase complex for lagging strand DNA replication. As such, these sequences are more frequently found on the lagging strand, meaning that they are biased to a single strand. As will be apparent to those skilled in the art, sequences complementary to these lagging strand biased sequences will be biased to the leading strand. By using leading strand biased sequences and their compliments, it is possible to obtain primer pairs with one member of each pair biased to either the leading or lagging strand.

Primer pairs are determined empirically, by constructing a matrix of the chosen oligonucleotide sequences and their compliments. For example, when 25 oligonucleotide sequences are used and one member of each primer pair is labeled, a 25 by 25 matrix can be constructed yielding 600 possible combinations of primers. When unlabeled primer pairs are used, a binary 25 by 2 binary matrix yielding 48 primer pairs is constructed. Primer pairs are tested using the polymerase chain reaction for their ability to produce the greatest number of amplification products. Primer pairs are then ranked according to their ability to produce the greatest number of resolvable amplification products. The exact number of primer pairs utilized will vary with the application. In general, approximately 25 primer pairs will provide complete coverage for a member of the *E. coli* species.

The size of the amplification products produced is not critically important. In one embodiment, primer pairs are chosen on their ability to produce the greatest number of amplification products containing 50 to 4500 bases. In another embodiment, primer pairs are chosen on the basis of their ability to produced amplification products containing 100 to 3000 bases. In yet another embodiment, primer pairs are chosen on the basis of their ability to produce amplification products containing 200 to 1500 bases.

Detection of the amplification products can be accomplished by use of reporter moieties. Reporter moieties can be incorporated directly into the amplification products, for example, by the use of labeled nucleotides. In one embodiment, nucleotides incorporating $^{32}P$, $^{33}P$ or $^{35}S$ are used in the amplification process. In another embodiment, nucleotides incorporating a variety of non-radioactive reporters such as fluorophores or fluorochromes, peptides, antibodies, antigens, vitamins or steroids can be used. Alternatively, reporter moieties, such as those previously described, can be incorporated into the primers which in turn become part of the amplification products. In another alternative, reporter moieties can be added to the 5' end of the primers. Any reporter moiety which capable of being linked to the 5' end of a primer can be used, for example radioactive labels, such as radionucleotides, fluorophores or fluorochromes, peptides, enzymes, antigens, antibodies, vitamins or steroids. In one preferred embodiment, the fluorophore IRD800 (Li-Cor, Inc., Lincoln Nebr.) is used. One or both members of a primer pair can be labeled. In one embodiment, the primer biased to the leading strand is labeled.

When large, generally greater than 100 Daltons, reporter moieties are attached to the 5' end of the primer, a spacer may be added to the 5' end of the primer. Without being bound by theory, spacers are thought to help prevent interference by the reporter moiety with binding of the primer to the template sequence. Spacers are preferably from 1 to 10 nucleotides in length, more preferably from 1 to 5 nucleotides in length and most preferably 2 nucleotides in length. In one preferred embodiment the nucleotide linker is AT. The spacer may be attached only to the primers which carry a reporter moiety on their 5' end, or the spacer can be added to both labeled and unlabeled primers.

Detection of polymorphism within the amplification products can be accomplished by any method known to those skilled in the art. More specifically, amplification products from different sources are compared to determine if the amplification products produced are identical or contain differences in one or more nucleotides due to nucleotide substitution, insertion or deletion. Differences in the amplification products can, for example, take the form of differences in product size, differences in product sequence, differences in quantity of each product produced, and differences in the number of amplification products produced.

In one preferred embodiment, polymorphism is detected on the basis of differences in size of the amplification products produced, for example, by electrophoresis through a suitable size fractionation medium. Separation by electrophoresis can be accomplished by polyacrylamide gel electrophoresis, agarose gel electrophoresis and capillary electrophoresis. When suitable conditions are employed, differences of a single nucleotide can be detected. In one preferred embodiment, size separation is accomplished by the use of denaturing polyacrylamide sequencing gels. Methods for making and running such gels are well known in the art. See for example, Ausubel et al., *Short Protocols in Molecular Biology,* 2nd ed., Greene Publishing, 1992; Sambrook et al., *Molecular Cloning,* 2nd ed., Cold Spring Harbor Laboratory Press, 1989; Davis et al., *Basic Methods in Molecular Biology,* Elsevier, 1986. In addition, precast sequencing gels can be obtained from a variety of commercial sources.

In some instances, simple inspection of the electrophoresis gels will be sufficient to detect polymorphisms that affect size, quantity and presence of the amplification product. In a preferred embodiment, polymorphisms detected can be quantified using densitometry, fluorometry or radiometry. In a particularly preferred embodiment, amplification products are detected using a Li-Cor 400 L automatic sequencer. Quantification is important where it is necessary to distinguish between homozygous and heterozygous polymorphisms.

In another embodiment, polymorphism is determined on the basis of hybridization. Under proper conditions, hybridization can detect single nucleotide substitutions. Hybridization methods useful in the present invention include Southern hybridization, dot blot hybridization, slot blot hybridization and the use of micro arrays. In one preferred embodiment, detection of polymorphism by hybridization is accomplished by the use of micro arrays. Methods for the production and use of micro arrays are well known in the art. See, *Nature Genetics Supplement,* Vol. Jan. 21, 1999. In general, nucleotide sequences are attached at known locations to a solid substrate such as microspheres or glass, nylon, polypropylene or silicone slides. Attachment of the sequences is accomplished by either direct synthesis of the sequence onto the substrate or by printing CDNA onto the substrate. Labeled amplification products are then incubated with the attached nucleotide sequences under conditions of high stringency. Polymorphism is detected by differences in the location and quantity of amplification products that hybridize on the array.

Polymorphism can also be detected by microscopic analysis. Labeled primers of the present invention or labeled amplification products produced using the present invention can be hybridized to chromosomes and their location determined. Differences in the location of the labeled primers or labeled amplification products can be used to determine polymorphism. In one preferred embodiment, the label used is a flourescent label. In this embodiment the location of the labeled primers or labeled amplification products can be determined by fluorescence microscopy using, for example, an epifluorescence microscope or a confocal microscope.

Polymorphism can also be detected by sequencing of the amplification products. When necessary, amplification products of interest can be further amplified by a second round of PCR to produce enough product for sequencing. Any sequencing method can be used with the present invention including those based on dideoxy sequencing (Sanger et al., *Proc. Natl. Acad. Sci., USA,* 74:5463–5467, 1977), chemical sequencing (Maxam and Gilbert, *Proc. Natl. Acad. Sci., USA,* 74:560–564, 1977) and hybridization sequencing (Drmanac et al., U.S. Pat. No. 5,695,940).

The method of the present invention has practical applications, including, but not limited to genetic mapping; determination of changes in expression patterns; the distinguishing and identification of the species, strain or serotype of organisms; and the identification of individuals?

Polymorphisms detected by the method of the present invention can be used to construct genetic linkage maps. For example, the presence or absence of amplification products obtained from samples from different organisms can be used to produce binary files. Phylogenetic relationships based on the pattern of amplification products obtained can be assessed through the maximum parsimony method and dendograms generated by Neighbor Joining (NJ) analysis (Saitou et al., *Mol. Biol. Evol.* 4:406–425, 1987). Thus, the present invention provides an improved method for the determination of evolutionary changes between related organisms. The present invention can also be used to identify nucleic acid segments involved in conferring pathogenicity, environmental fitness or economically important traits.

Further, the method of the present invention can be used to identify the species, strain or serotype of organisms such as bacteria. Using the method of the present invention, a data base can be constructed based on the pattern of amplification products characteristic of known species, strains or serotypes. The pattern of amplification products obtained from an unknown organism using the present invention can be compared to the patterns in the data base, thereby allowing identification of the organism.

The present invention can also be used for the identification of individuals. Using the method of the present invention, a data base can be constructed containing the pattern of amplification products of individuals. The pattern of amplification products obtained from an unknown individual using the present invention can be compared to the patterns in the data base, thereby allowing identification of the individual.

The present invention is also useful for differential display analysis for the identification of genes by their expression patterns. Using the method of the present invention, amplification products can be produced from DNA prepared by reverse transcription of RNA extracted from two groups of organisms that are, for example, at differing stages of development, have been subjected to different environmental conditions, or other conditions which may alter gene expression. As discussed previously, the amplification products produced can include a reporter moiety. The amplification products can be detected by any of the methods previously discussed including, but not limited to electrophoresis and hybridization. Detection can be binomial (presence/absence) or it can be quantitative. Examples of suitable quantitative methods include densitometry, fluorometry and radiometry. By examining differences in the pattern of amplification products produced, it is possible to identify unique genes whose expression is regulated by the particular condition of interest.

Another embodiment of the present invention includes a kit for the detection of nucleic acid polymorphisms and the identification of organisms by amplification of nucleic acid sequences using primers based on over represented oligonucleotide sequences. The kit comprises at least one pair of oligonucleotide primers. Each primer pair consists of a first oligonucleotide primer based on an over represented oligonucleotide sequence biased to a first strand of DNA and a second oligonucleotide primer based on a different over represented oligonucleotide sequence biased to a strand of DNA complementary to the first strand of DNA. It will be apparent to those skilled in the art that the kit can contain more that one pair of primers. In a preferred embodiment, the kit contains multiple primer pairs.

Also included in the kit is a reaction solution comprising a buffer and a source of magnesium ions ($Mg^{2+}$). Any suitable buffer can be used. In a preferred embodiment the buffer is Tris-HCl. The optimal concentration of buffer will vary with reaction conditions and must be determined empirically. In general, the concentration of Tris-HCl will vary between 10 mM and 100 mM. In one embodiment, the concentration of Tris-HCl is 50 mM. The pH of the reaction solution will generally vary between 6 and 11 and must be optimized for each set of reaction conditions. In one embodiment, the pH of the reaction solution is 9.3. Any source of magnesium ions is also suitable. In one embodiment, the source of magnesium ions is a magnesium salt, in another embodiment the source of magnesium ions is a halide salt of magnesium and in yet another embodiment, the source of magnesium ions is magnesium chloride. As is known to those skilled in the art, the concentration of magnesium ion will vary with the reaction conditions. In general, the reaction will contain 0.5 to 5 mM magnesium over the total deoxynucleotide triphosphates (dNTPs) concentration. In one embodiment, the reaction contains 4 mM $MgCl_2$.

The kit also includes instructions for using the kit. Such instructions can include information on conducting amplification reactions using the kit components, detection of amplification products and use of the information obtained to determine nucleic acid sequence polymorphism, genetic relatedness of different organisms, or the identity of unknown organisms.

The kit may also include additional components for conducting amplification reactions and detection of amplification products. For example, the kit may contain deoxynucleotide triphosphates (dNTPs). The dNTPs (dATP, dCTP, dGTP, dTTP) can be provided either individually or as a mixture containing all four dNTPs. When provided as a mixture, it is preferred that the mixture contain equal amounts of each dNTP. The concentration of dNTPs will vary depending on the reaction conditions. In general, the concentration for each dNTP will vary between 10 $\mu$M and 1 mM. In one embodiment, the concentration of each dNTP is 750 $\mu$M.

The kit may also contain at least one nucleic acid polymerase. In a preferred embodiment, a thermal stable nucleic acid polymerase is included in the kit and more particularly a thermal stable DNA polymerase. When the starting nucleic acid template is RNA, the kit may additionally contain a reverse transcriptase in addition to a DNA polymerase.

The kit may also contain a reporter moiety for the detection of amplification products. The reporter moiety can be incorporated into one or all of the dNTPs or may be incorporated into one of both members of each primer pair either through the use of labeled nucleotides or by attachment of reporter moiety to the 5' end of the primer. Suitable reporter moieties include, but radioactive labels, such as radionuclides, fluorophores or fluorochromes, peptides, enzymes, antigens, antibodies, vitamins or steroids. Additionally, the reporter moiety can be a nucleic acid intercalating dye.

The form in which the kit components are provided is not critically important. For example, components may be provided in solution, dried, lyophilized, or frozen form and may be concentrated or ready for use. If supplied in a concentrated, dried or lyophilized form, a suitable diluent may also be included in the kit.

In yet another embodiment of the present invention, polymorphisms can be detected in a nucleic acid sequence by using nucleotide sequences comprising over represented oligonucleotides to "paint" chromosomes(Guan et al., *Genomics*, 22:101–107, 1994; Christian et al., *Mamm. Genome*, 10:628–631, 1999). The nucleotide sequences used can be the over represented oligonucleotides themselves, complements of the over represented oligonucleotides, or nucleotide sequences containing the over represented oligonucleotides or their complements.

Nucleotide sequences used to paint chromosomes are made based on over represented oligonucleotides. The nucleotide sequences can be naturally occurring and produced by restriction enzyme digestion or can be synthesized by methods known to those of ordinary skill in the art such as by chemical synthesis or the polymerase chain reaction (See, Davis et al., *Basic Methods in Molecular Biology*, Elsevier, 1986; Innis et al., *PCR Protocols*, Academic Press, 1990; Sambrook et al., *Molecular Cloning*, 2nd ed., Cold Spring Harbor Laboratory Press, 1989). Additionally, the nucleotide sequences comprise a reporter moiety. In one preferred embodiment, the reporter moiety is a fluorochrome.

Metaphase chromosome spreads are obtained by standard methods (See, Guan et al., *Genomics*, 22:101–107, 1994; Christian et al., *Mamm. Genome*, 10:628–631, 1999). Metaphase spreads are denatured in 70% formamide/2× SSC, pH 7.0 for 3 minutes followed by successive washes in 70%, 85% and 100% ethanol for 3 minutes each. Nucleotide sequences are added to a hybridization mix containing 50% formamide, 2×SSC, 10% dextran and 3 $\mu$g of blocking DNA per 15 $\mu$l. The nucleotide sequence in the hybridization mix is denatured by heating to 70° C. for 5 minutes and then applied to the chromosome spreads. Hybridization is generally conducted over an approximately 12 hour period at 37° C.

After hybridization, unbound nucleotide sequences are removed by three, 5 minute washes in 50% formamide, 2×SSC, pH 7.0 at 45° C. If desired, chromosomes can be counter stained to aid in visualization. In one preferred embodiment, chromosomes are counter stained with DAPI. Chromosome spreads are then examined by microscopy. In one preferred embodiment, the reporter moiety used is a fluorochrome and fluorescence microscopy is used, for example, epi fluorescence microscopy or confocal fluorescence microscopy. In another preferred embodiment, the microscope system used includes a computer assisted image analysis system.

Polymorphism is detected on the basis of differences in the locations where the nucleotide sequences hybridize on chromosomes obtained from different sources. In addition, the pattern of binding locations of the nucleotide sequences to the chromosomes can be used to identify the species, serotype or strain of an organism by comparing the pattern obtained to patterns that identify the species and patterns unique to certain serotypes or strains. Further, the method can be use to identify individuals by comparing to pattern obtained to previously obtained patterns in a database.

EXAMPLES

Primer Design

Primers used were based on 23 over represented octamers in the *E. coli* K-12 genome (Salzberg et al., *Gene*, 217:57–67, 1998; Blattner et al., *Science* 277:1453–1462, 1997). Table 1. The use of 23 octamers resulted in 506 possible primer combinations (23 leading strand octamers× 23 lagging strand complements—23 pairs of leading strand octamers and their own complements). Of these, 70 pairs were arbitrarily chosen and tested on a set of two *E. coli* O157:H7 strains (FRIK 1641 and FRIK 533) (Gouveia et al., *J. Clin. Microbiol.*, 36:727–733, 1998) and strains from the ECOR collection (ECOR 20 and ECOR 50) (Ochman and Selander, *J. Bacteriol.*, 157:690–693, 1984). One primer in each pair was labeled on its 5' end with a fluorochrome that emits in the near infrared region of the spectrum (IRD800, Li-Cor, Inc., Lincoln, Nebr.). Each primer pair consisted of a fluorescent primer based on an octamer biased to the leading strand and an unlabeled primer based on a second octamer biased to the lagging (complementary) strand (i.e. the complement to a leading strand octamer). Due to the possible effect of the presence of a 5' fluorochrome on annealing of the octamers, an AT dinucleotide was added to the 5' end of each primer. Primer pairs were chosen based on the number of bands (amplification products) within a 200 to 1,500 base window.

TABLE 1[a]

| Leading Strand Octamers | |
|---|---|
| K12OCT1 | CGCTGGCG (Seq. No. 1) |
| K12OCT2 | GGCGCTGG (Seq. No. 2) |
| K12OCT3 | GCTGGTGG (Seq. No. 3) |
| K12OCT4 | GCTGGCGG (Seq. No. 4) |

TABLE 1a-continued

Leading Strand Octamers

| | | |
|---|---|---|
| K12OCT5 | TGCTGGCG | (Seq. No. 5) |
| K12OCT6 | GCGCTGGC | (Seq. No. 6) |
| K12OCT7 | TGGCGCTG | (Seq. No. 7) |
| K12OCT8 | GCTGGCGC | (Seq. No. 8) |
| K12OCT10 | CGCTGGTG | (Seq. No. 9) |
| K12OCT12 | CTGGCGGC | (Seq. No. 10) |
| K12OCT13 | CTGGCGCA | (Seq. No. 11) |
| K12OCT14 | GCTGGCGA | (Seq. No. 12) |
| K12CCT15 | TGGCGGCG | (Seq. No. 13) |
| K12OCT18 | AACTGGCG | (Seq. No. 14) |
| K12OCT19 | GCTGGAAG | (Seq. No. 15) |
| K12OCT20 | CTGGCGCG | (Seq. No. 16) |
| K12OCT21 | GCGCTGGA | (Seq. No. 17) |
| K12OCT22 | CTGGCGAA | (Seq. No. 18) |
| K12OCT23 | TGCTGGTG | (Seq. No. 19) |
| K12OCT25 | CTGGTGGT | (Seq. No. 20) |
| K12OCT26 | CTGGTGGC | (Seq. No. 21) |
| K12OCT27 | CGGTGGCG | (Seq. No. 22) |
| K12OCT28 | TGCGCTGG | (Seq. No. 23) |
| K12OCT1C | CGCCAGCG | (Seq. No. 24) |
| K12OCT2C | CCAGCGCC | (Seq. No. 25) |
| K12OCT3C | CCACCAGC | (Seq. No. 26) |
| K12OCT4C | CCGCCAGC | (Seq. No. 27) |
| K12OCT5C | CGCCAGCA | (Seq. No. 28) |
| K12OCT6C | GCCAGCGC | (Seq. No. 29) |
| K12OCT7C | CAGCGCCA | (Seq. No. 30) |
| K12OCT8C | GCGCCAGC | (Seq. No. 31) |
| K12OCT10C | CACCAGCG | (Seq. No. 32) |
| K12OCT12C | GCCGCCAG | (Seq. No. 33) |
| K12OCT13C | TGCGCCAG | (Seq. No. 34) |
| K12OCT14C | TCGCCAGC | (Seq. No. 35) |
| K12OCT15C | CGCCGCCA | (Seq. No. 36) |
| K12OCT18C | CGCCAGTT | (Seq. No. 37) |
| K12OCT19C | CTTCCAGC | (Seq. No. 38) |
| K12OCT20C | CGCGCCAG | (Seq. No. 39) |
| K12OCT21C | TCCAGCGC | (Seq. No. 40) |
| K12OCT22C | TTCGCCAG | (Seq. No. 41) |
| K12OCT23C | CACCAGCA | (Seq. No. 42) |
| K12OCT25C | ACCACCAG | (Seq. No. 43) |

TABLE 1a-continued

Leading Strand Octamers

| | | |
|---|---|---|
| K12OCT26C | GCCACCAG | (Seq. No. 44) |
| K12OCT27C | CGCCACCG | (Seq. No. 45) |
| K12OCT28C | CCAGCGCA | (Seq. No. 46) | aAll primer sequences are listed 5' to 3'

Of the 70 pairs tested, 18 produced over 200 bands, 43 produced between 150 and 200 bands, and 9 produced less than 150 bands. Six of the 61 pairs that generated between 150 to 250 resolvable bands were chosen for further characterization based on maximum discrimination of the E. coli O157:H7 strains from the ECOR strains. The fluorescently labeled leading strand primers chosen where as follows:
ATGCTGGTGG (Seq. No. 47)
ATGCTGGCGG (Seq. No. 48)
ATTGGCGCTG (Seq. No. 49)
ATGCTGGCGA (Seq. No. 50)
ATGCGCTGGA (Seq. No. 51)
ATCTGGCGAA (Seq. No. 52)

The unlabeled lagging strand primers chosen had the following sequences:
ATCGCCAGCG (Seq. No. 53)
ATCCGCCAGC (Seq. No. 54)
ATGCCAGCGC (Seq. No. 55)
ATGCGCCAGC (Seq. No. 56)
ATTGCGCCAG (Seq. No. 57)
ATCTTCCAGC (Seq. No. 58)

Genome Scanning

Amplification reactions were conducted in a volume of 20 μl. Each reaction contained 50 ng of chromosomal DNA, 0.5 pmol of each primer, 750 μM dNTPs, 50 mM Tris, pH 9.3, 4 mM $MgCl_2$, and 0.5 units of a thermal stable DNA polymerase (SequiTherm™, Epicentre, Madison, Wis.). The amplification protocol used was denaturation at 95° C. for 2 minutes followed by 30 cycles of 25° C. for 10 seconds, ramp to 40° C. at 1° C./4 seconds, 40° C. for 15 seconds, 72° C. for 30 seconds and 95° C. for 15 seconds.

After completion of the cycling, an equal volume of loading dye (0.012% bromphenol blue, 0.1 mM EDTA, pH 8.0 in 100% formamide) was added to each reaction. A portion (1 μl) of each reaction was loaded onto 4% denaturing polyacrylamide gels, (66 cm gel length) in a Li-Cor 4000 automated sequencer (Li-Cor, Inc., Lincoln, Nebr.). Fragment length was calculated from molecular weight markers run alongside the reactions.

TABLE 2

| Primer Paira | No. of Bandsb | Lengthc |
|---|---|---|
| Seq. No. 47–Seq. No. 54 | 186 | 165,155 |
| Seq. No. 48–Seq. No. 58 | 245 | 227,178 |
| Seq. No. 49–Seq. No. 56 | 235 | 215,356 |
| Seq. No. 50–Seq. No. 53 | 167 | 174,872 |
| Seq. No. 51–Seq. No. 57 | 189 | 161,173 |
| Seq. No. 52–Seq. No. 55 | 165 | 154,268 |
| Total | 1,187 | 1,098,002 | aThe first primer in each pair was labeled.
bTotal number of bands resolved between 200 and 1500 bases in length from E. coli O157:H7 strain FRIK 1641.
cCombined sizes, in bases, of band resolved between 200 and 1500 bases in length.

The combined length of the amplification products produced using six primer pairs by the method of the present invention was obtained by measuring the length of the individual amplification products within the 200 to 1500 bp window using RFLPScan (Scanalytics, Inc. Fairfax, Va.). The combined lengths for the amplification products from *E. coli* O157:H7 strain FRIK 1641 is shown in Table 2. The six primer pairs provided a range of coverage from 154,268 bases (Seq. No. 47–Seq. No. 54) to 227,178 bases (Seq. No. 48–Seq. No. 58). Together, the amplification products produced by the method of the present invention provided an estimated 1,098,002 bases for comparative analysis. This estimate does not account for redundancy resulting from overlapping products in regions of closely spaced octamers.

Determination of Genetic Relationships

Organisms from within a limited geographic region. Studies on a characterized strain set derived from dairy cattle and humans within a three-county region of Wisconsin were conducted. Human isolates in this set were derived from sporadic cases (FRIK 523 through FRIK 579) and an outbreak of hemorrhagic colitis at a daycare center (FRIK 583 through FRIK 856) that occurred during 1994 (Gouveia et al., *J. Clin. Microbiol.* 36:727–733, 1998). Cattle isolates (FRIK 920 through FRIK 1641) were derived from a 1995–1996 longitudinal study of three dairy cattle farms in this same region (Shere et al., *Appl. Environ. Microbiol.* 64:1390–1399, 1998).

Analysis using the method of the present invention was performed on each isolate using the six different primer combinations described above. Binary files were created in Microsoft Excel 97® from printed copies of the images produced by an Alden 9315CTP photographic quality thermal printer (Alden Electronics, Inc., Westborough, Mass.). The files were generated from the presence/absence of bands (FIG. 1) between 200–1500 bases in length and binary files from each primer pair were combined head to tail in Microsoft Word 97®. Phylogenetic relationships based on the amplification products were assessed through maximum parsimony methods in PAUP V.4.0 (Swofford, PAUP version 4, Sinauer Associates, Sunderland, Mass.) and by Neighbor Joining (NJ) analysis (Saitou et al., *Mol. Biol. Evol.* 4:406–425, 1987), both of which yielded similar results. The *E. coli* K-12 strain MC1061, which is phylogenetically distant from *E. coli* O157:H7 was included in each analysis as an outgroup to assess the ancestral state of the characters as described (Boerlin et al., *Infect. Immun.* 66:2553–2561, 1998). The O157:H7 strain ATCC43895 (EDL933) was included as a standard O157:H7 strain.

Of 1,251 amplification products scored from this strain set, 191 segments were variable among the O157:H7 strains, indicating that within this limited geographic region, a considerable amount of genomic diversity can be observed by the method of the present invention. Of these variable segments, 140 were parsimony-informative.

Figure 2:
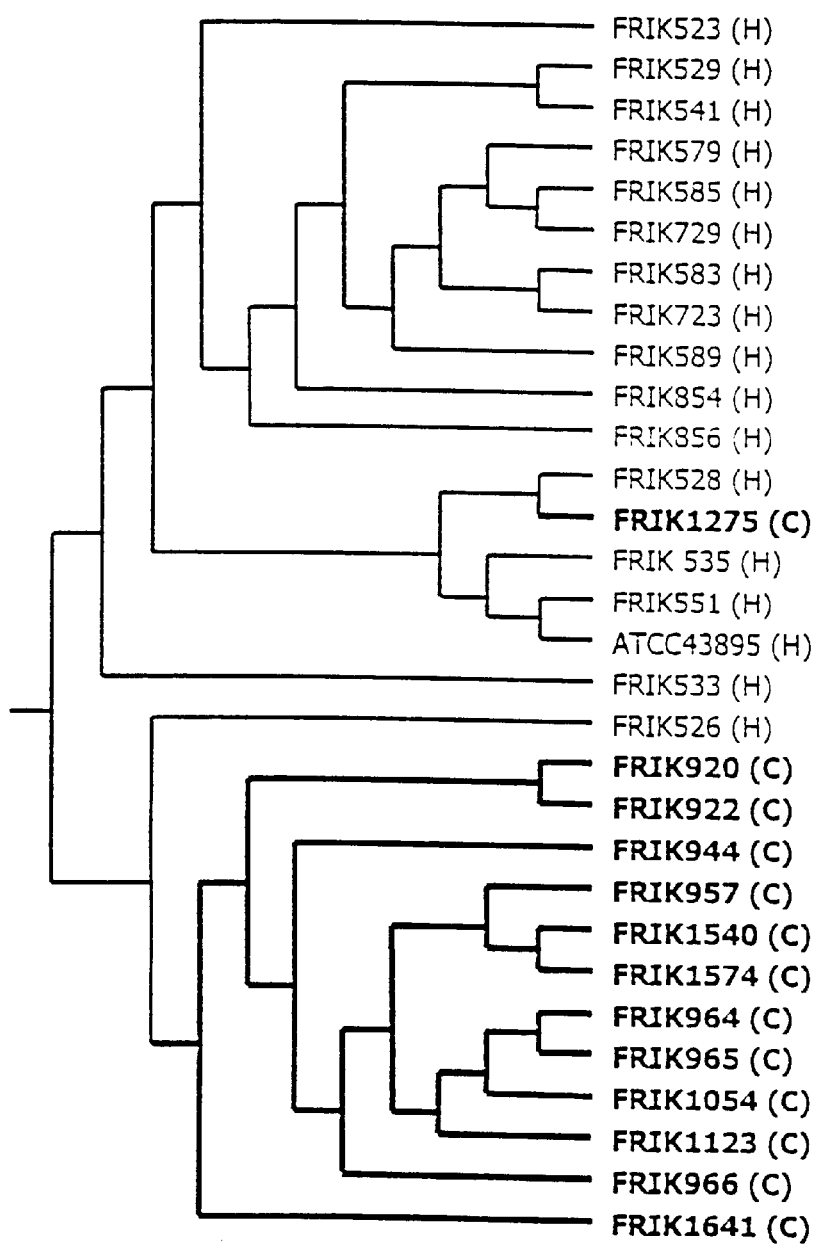
FIG. 2 shows a dendogram produced by Neighbor Joining (NJ) analysis of binary files representing the presence and absence of 1,251 amplification products from each strain produced with six different primer combinations and the method of the present invention (tree length=960, consistency index=0.74, retention index=0.83 with 168 characters). The tree is rooted with the K-12 derivative MC 1061 as an outgroup. Among the O157:H7 strains, 1,060 of the 1,252 characters were conserved. Human isolates (H) and cattle isolates (C) have been previously described (Shere et al., *Appl. Environ. Microbiol.* 64:1390–1399, 1998; Gouveia et al., *J. Clin. Microbiol.* 36:727–733, 1998).

A dendogram obtained by NJ analysis (FIG. 2) demonstrated that the strains constituted a monophyletic lineage that has diverged into two distinct populations, one containing primarily human isolates and the other containing primarily cattle isolates. These results suggest that a substantial portion of the *E. coli* O157:H7 strains isolated from cattle may comprise a genetically distinct population that is not commonly isolated from human cases of hemorrhagic colitis. However, because the cattle herds are regionally confined and human isolates could have originated from food sources outside of this region, it remained possible that the limited geography of strain sampling influenced the distribution.

Figure 3:
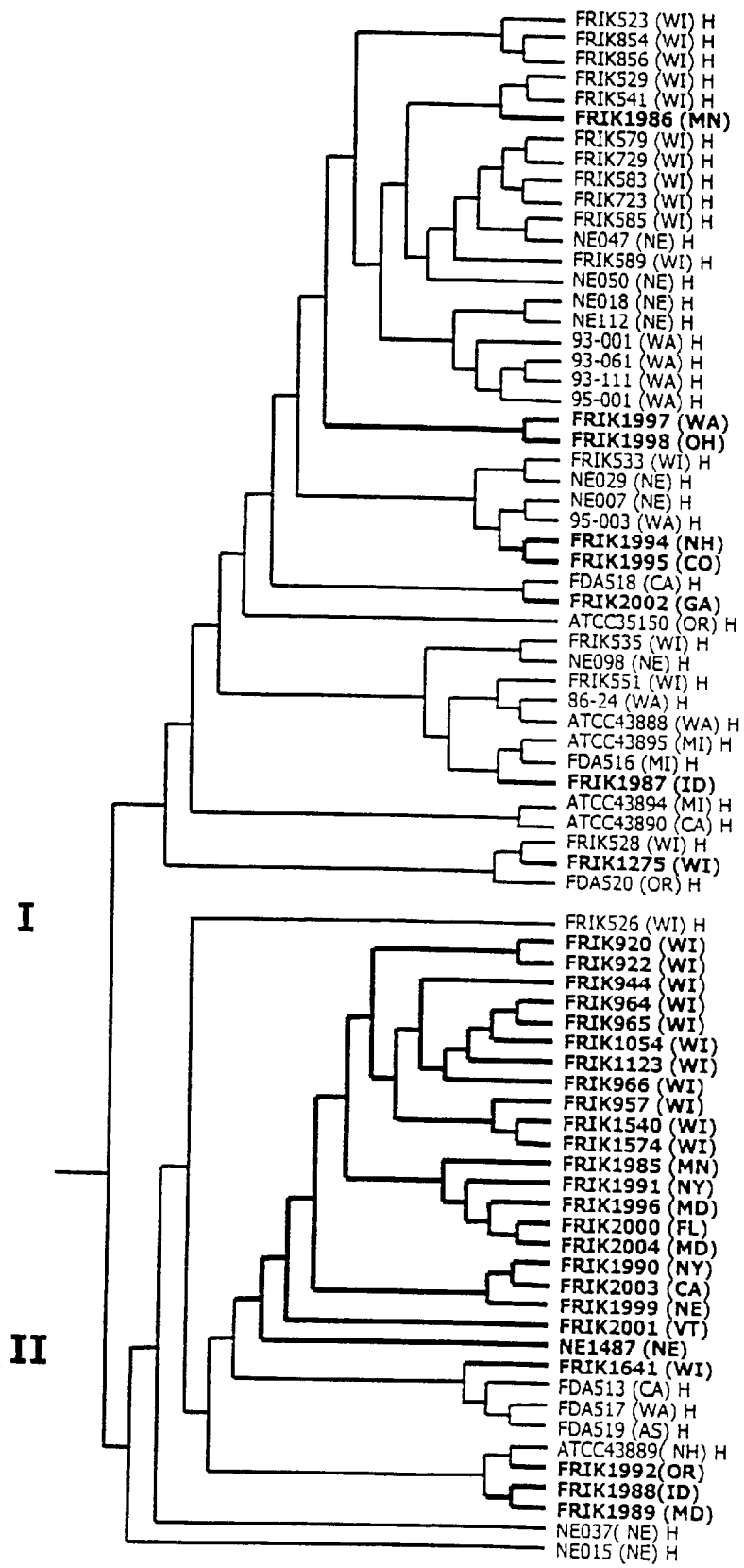
FIG. 3 shows a dendogram produced by Neighbor Joining (NJ) analysis of binary files representing the presence and absence of 1,250 amplification products from each strain produced with six different primer combinations and the method of the present invention (tree length=1398, consistency index=0.61, retention index=0.81 with 235 characters. Among the O157:H7 strains, 892 of the 1,250 bands were conserved. The tree is rooted using the K-12 derivative MC 1061 as an outgroup. The state from which each strain originated is indicated by the two letter abbreviation in parentheses. Human isolates have an H at the end of the designation and bovine isolates are in bold.

Geographically distributed organisms. To determine if geography biased the results of the previous example, human and bovine isolates from a broader geographic region were analyzed using the method of the present invention. Additional cattle isolates for these experiments were obtained from a collection of isolates from a 1991–1992 prevalence study of *E. coli* O157:H7 in dairy cattle herds across the nation (Lee, et al., *Vet. Microbiol.* 48:223–230, 1996). The isolates were derived from 16 different states, including MN, ID, MD, NY, OR, TN, NH, CO, WI, WA, OH, NE, FL, VT, GA, and CA. Additional human isolates, collected from outbreaks and sporadic cases of hemorrhagic colitis cases in AK, OR, CA, MT, MI, NE, NC, WA, and WI during the years 1982–1998 were also included. Using the same primer combinations described above, 1,250 amplification products from this strain set were evaluated (FIG. 3). In this geographically and temporally dispersed strain set, only 892 amplification products were conserved among the O157:H7 strains. Of the 358 variable segments, 223 were parsimony informative. Thus, the genomic diversity of the strains increased with geographic and temporal distribution as would be expected; however, the relationship of the strains was more informative.

Consistent with the findings from the previous Wisconsin set, NJ analysis of this geographically and temporally dispersed strain set (FIG. 3) demonstrated the existence of two distinct lineages (I and II). Bovine isolates from geographically unlinked locations were highly related to the large set of bovine isolates from Wisconsin and constituted the majority of strains in lineage II, indicating that this clade is not regionally specific. The absence of human isolates within the clade suggests that this population is not readily transmitted to humans or is not readily capable of causing disease. In fact, the scant representation of human isolates among lineage II suggests that the entire lineage may be impaired in transmissibility to or pathogenicity in humans.

In contrast to lineage II strains, most bovine isolates in lineage I were dispersed among the lineage and related to human isolates, as would be expected since contaminated beef is one source for transmission of *E. coli* O157:H7 to humans. Assuming the bovine isolates from the National Animal Health Monitoring Systems survey (FRIK1985 through FRIK2004) are representative of distribution of the two lineages in the U.S., these results predict that only one third (7/20) of bovine isolates belong to the apparently more pathogenic lineage I. The results of this study demonstrate the usefulness of the present invention for identification of polymorphic markers that discriminate between subpopulations of microorganisms.

In light of the detailed description of the invention and the examples presented above, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventors do not intend to be bound by those conclusions and functions, but put them forth only as possible explanations.

It is to be further understood that the specific embodiments of the present invention as set forth are not intended as being exhaustive or limiting of the invention, and that many alternatives, modifications, and variations will be apparent to those skilled in the art in light of the foregoing examples and detailed description. Accordingly, this invention is intended to embrace all such alternatives, modifications, and variations that fall within the spirit and scope of the following claims.

What is claimed is:

1. A method for determining polymorphism in a DNA sequence on the basis of nucleotide differences comprising, a) amplifying said DNA sequence to produce amplification products using at least one pair of oligonucleotide primers, said primer pair comprising, i) a first primer that binds to a first over represented oligonucleotide biased to one strand of said DNA, and ii) a second primer that binds to a second over represented oligonucleotide biased to a DNA strand complementary to the strand in i), b) in a separate reaction, repeating a) for at least one other DNA sequence from another source, c) analyzing the amplification products by a method capable of detecting differences in nucleic acid sequences, and d) comparing the results obtained for each nucleic acid sequence.

2. The method of claim 1 wherein the DNA is genomic DNA or cDNA.

3. The method of claim 1 wherein the DNA is obtained by reverse transcription of RNA.

4. The method of claim 1 wherein the DNA is obtained from a microorganism.

5. The method of claim 4 wherein the microorganism is *E. coli*.

6. The method of claim 1 wherein the over represented oligonucleotide is between 6 and 30 bases in length.

7. The method of claim 6 wherein the over represented oligonucleotide is 8 bases in length.

8. The method of claim 4 wherein the primers are selected from the group consisting of Seq. No. 1, Seq. No. 2. Seq. No. 3, Seq. No. 4, Seq. No. 5, Seq. No. 6, Seq. No. 7, Seq. No. 8, Seq. No. 9, Seq. No. 10, Seq. No. 11, Seq. No. 12, Seq. No. 13, Seq. No. 14, Seq. No. 15, Seq. No. 16, Seq. No. 17, Seq. No. 18, Seq. No. 19, Seq. No. 20, Seq. No. 21, Seq. No. 22, Seq. No. 23, Seq. No. 24, Seq. No. 25, Seq. No. 26, Seq. No. 27, Seq. No. 28, Seq. No. 29, Seq. No. 30, Seq. No. 31 Seq. No. 32, Seq. No. 33, Seq. No. 34, Seq. No. 35, Seq. No. 36, Seq. No. 37, Seq. No. 38, Seq. No. 39, Seq. No. 40, Seq. No. 41, Seq. No. 42, Seq. No. 43, Seq. No. 44, Seq. No. 45 and Seq. No. 46.

9. The method of claim 1 further comprising incorporating at least one reporter moiety into the amplification products.

10. The method of claim 9 wherein the reporter moiety is incorporated into at least one primer.

11. The method of claim 9 or 10 wherein the reporter moiety is selected from the group consisting of radionuclides, fluorochromes, peptides, enzymes, antigens, antibodies, vitamins, steroids and dyes.

12. The method of claim 1 wherein the detection of differences in nucleic acid sequences is determined by a method selected from the group consisting of electrophoresis, hybridization, and sequencing.

13. A method for identifying an organism by species, serotype, or strain comprising:
   a) obtaining DNA from the organism, said DNA comprising over represented oligonucleotide sequences,
   b) amplifying said DNA to produce amplification products using at least one pair of oligonucleotide primers, said primer pair comprising,
      i) a first primer that binds to a first over represented oligonucleotide biased to one strand of said DNA, and
      ii) a second primer that binds to a second over represented oligonucleotide biased to a DNA strand complementary to the strand in i),
   c) analyzing the amplification products by a method capable of detecting differences in nucleic acid sequences, and
   d) analyzing the results obtained in c) for amplification products in common with all members of the species and for products unique to strains or serotypes within the species and comparing the results to a database of previously analyzed products, thereby identifying the species, serotype or strain of the organism.

14. A method for identifying an individual comprising:
   a) obtaining DNA from said individual, said DNA comprising over represented oligonucleotide sequences,
   b) amplifying said DNA to produce amplification products using at least one pair of oligonucleotide primers, said primer pair comprising,
      i) a first primer that binds to a first over represented oligonucleotide biased to one strand of said DNA, and
      ii) a second primer that binds to a second over represented oligonucleotide biased to a DNA strand complementary to the strand in i),
   c) analyzing the amplification products by a method capable of detecting differences in nucleic acid sequences, and
   d) comparing the results obtained in c) to a database of previously analyzed products, thereby identifying the individual.

15. The method of claim 13 or 14 wherein the DNA is selected from the group consisting of genomic DNA and cDNA.

16. The method of claim 13 or 14 wherein the DNA is obtained by reverse transcription of RNA into DNA.

17. The method of claim 13 wherein the organism is a microorganism.

18. The method of claim 17 wherein the microorganism is an *E. coli*.

19. The method of claim 13 or 14 wherein the over represented oligonucleotide is between 6 and 30 bases in length.

20. The method of claim 19 wherein the over represented oligonucleotide is 8 bases in length.

21. The method of claim 17 wherein the primers are selected from the group consisting of Seq. No. 1, Seq. No. 2. Seq. No. 3, Seq. No. 4, Seq. No. 5, Seq. No. 6, Seq. No. 7, Seq. No. 8, Seq. No. 9, Seq. No. 10, Seq. No. 11, Seq. No. 12, Seq. No. 13, Seq. No. 14, Seq. No. 15, Seq. No. 16, Seq. No. 17, Seq. No. 18, Seq. No. 19, Seq. No. 20, Seq. No. 21, Seq. No. 22, Seq. No. 23, Seq. No. 24, Seq. No. 25, Seq. No. 26 Seq. No. 27, Seq. No. 28, Seq. No. 29, Seq. No. 30, Seq. No. 31, Seq. No. 32, Seq. No. 33, Seq. No. 34, Seq. No. 35, Seq. No. 36, Seq. No. 37, Seq. No. 38, Seq. No. 39, Seq. No. 40, Seq. No. 41, Seq. No. 42, Seq. No. 43, Seq. No. 44, Seq. No. 45 and Seq. No. 46.

22. The method of claim 13 or 14 further comprising incorporating at least one reporter moiety into the amplification products.

23. The method of claim 22 wherein the reporter moiety is incorporated into at least one primer.

24. The method of claim 22 wherein the reporter moiety is selected from the group consisting of radionuclides, fluorophores, peptides, enzymes, antigens, antibodies, vitamins, steroids and dyes.

25. The method of claim 13 or 14 wherein the detection of differences in nucleic acid sequences is determined by a method selected from the group consisting of electrophoresis, hybridization, and sequencing.

26. A method for identifying genes by differential display analysis comprising:
   a) isolating mRNA from two groups of organisms,
   b) converting the mRNA to DNA by reverse transcription,
   c) amplifying said DNA to produce amplification products using at least one pair of oligonucleotide primers, said primer pair comprising,
      i) a first primer that binds to a first over represented oligonucleotide biased to one strand of said DNA, and
      ii) a second primer that binds to a second over represented oligonucleotide biased to a DNA strand complimentary to the strand in i),
   d) detecting the amplification products produced by a method capable of detecting the presence of said amplification products, and e) determining pattern differences in the amplification products produced.

27. The method of claim 26 wherein the organisms are microorganisms.

28. The method of claim 27 wherein the microorganisms are *E. coli*.

29. The method of claim 26 wherein the over represented oligonucleotide is between 6 and 30 bases in length.

30. The method of claim 29 wherein the over represented oligonucleotide is 8 bases in length.

31. The method of claim 27 wherein the primers are selected from the group consisting of Seq. No. 1, Seq. No. 2. Seq. No. 3, Seq. No. 4, Seq. No. 5, Seq. No. 6, Seq. No. 7, Seq. No. 8, Seq. No. 9, Seq. No. 10, Seq. No. 11, Seq. No. 12, Seq. No. 13, Seq. No. 14, Seq. No. 15, Seq. No. 16, Seq. No. 17, Seq. No. 18, Seq. No. 19, Seq. No. 20, Seq. No. 21, Seq. No. 22, Seq. No. 23, Seq. No. 24, Seq. No. 25, Seq. No. 26, Seq. No. 27, Seq. No. 28, Seq. No. 29, Seq. No. 30, Seq. No. 31 Seq. No. 32, Seq. No. 33, Seq. No. 34, Seq. No. 35, Seq. No. 36, Seq. No. 37, Seq. No. 38, Seq. No. 39, Seq. No. 40, Seq. No. 41, Seq. No. 42, Seq. No. 43, Seq. No. 44, Seq. No. 45 and Seq. No. 46.

32. The method of claim 26 further comprising incorporating at least one reporter moiety into the amplification products.

33. The method of claim 32 wherein the reporter moiety is incorporated into at least one primer.

34. The method of claim 32 or 33 wherein the reporter moiety is selected from the group consisting of radionuclides, fluorophores, peptides, enzymes, antigens, antibodies, vitamins, steroids and dyes.

35. The method of claim 26 wherein the detection of the amplification products produced is by a method selected from the group consisting of electrophoresis and hybridization.

36. The method of claim 26 wherein the detecting method is a quantitative method.

37. The method of claim 36 wherein the quantitative detecting method is selected from the group consisting of densitometry, fluorometry, and radiometry.

38. A kit comprising:
   a) at least one pair of oligonucleotide primers, said primer pair comprising,
      i) a first primer that binds to a first over represented oligonucleotide biased to one strand of DNA, and
      ii) a second primer that binds to a second over represented oligonucleotide biased to a DNA strand complementary to the strand in i),
   b) a reaction solution comprising a buffer and a magnesium salt, and
   c) instructions for amplification of nucleic acid sequences using the at least one set of primers pairs to produce amplification products and for detection of nucleic acid sequence polymorphism from said amplification products.

39. The kit of claim 38 further comprising dATP, dTTP, dGTP and dCTP.

40. The kit of claim 38 further comprising at least one nucleic acid polymerase.

41. The kit of claim 40 wherein at least one of the at least one nucleic acid polymerase is a thermal stable polymerase.

42. The kit of claim 39 wherein at least one of dATP, dTTP, dGTP and dCTP further comprise a reporter moiety.

43. The kit of claim 38 wherein at least one member of the at least one primer pair further comprises a reporter moiety.

44. The kit of claim 42 or 43 wherein the reporter moiety is selected from the group consisting of radionuclides, fluorophores, peptides, enzymes, antigens, antibodies, vitamins, steroids and dyes.

45. A method for the determination of polymorphism in a DNA sequence comprising:
   a) producing an oligonucleotide sequence containing a reporter moiety, said oligonucleotide comprising an over represented oligonucleotide,
   b) if desired, repeating step a) at least once to produce at least one additional oligonucleotide sequence containing a reporter moiety, said additional oligonucleotide sequence comprising a different over represented oligonucleotide,
   c) contacting the oligonucleotide of a) and if present b) with chromosomes obtained from an organism, so that the oligonucleotide hybridizes to complementary nucleotide sequences contained in said chromosomes,
   d) repeating c) with chromosomes obtained from a different organism,
   e) detecting the presence of the oligonucletides on the chromosomes, and
   f) comparing the locations of the oligonucleotides on the chromosomes to detect polymorphism.

46. The method of claim 45 wherein the polymorphism detected is used to identify individuals.

47. The method of claim 45 wherein the reporter moiety is selected from the group consisting of radionuclides, fluorochromes, peptides, enzymes, antigens, antibodies, vitamins, steroids and dyes.

48. The method of claim 45 wherein the reporter moiety is a fluorochrome.

49. The method of claim 45 wherein the location of the oligonucleotide is detected by microscopy.

50. The method of claim 49 wherein the location of the oligonucleotide is detected by fluorescence microscopy.

51. The method of claim 49 wherein the location of the oligonucleotide is detected by confocal microscopy.

* * * * *

UNITED STATES PATENT AND TRADEMARK OFFICE
CERTIFICATE OF CORRECTION

PATENT NO. : 6,284,466 B1  Page 1 of 1
APPLICATION NO. : 09/398499
DATED : September 4, 2001
INVENTOR(S) : Andrew Benson It is certified that error appears in the above-identified patent and that said Letters Patent is hereby corrected as shown below:

Column 1 at line 10 insert the following phrase, --This invention was made with government support under grant 98-35201-6215 awarded by the United States Department of Agriculture. The government has certain rights in the invention.--

Signed and Sealed this

Eighteenth Day of March, 2008

JON W. DUDAS
*Director of the United States Patent and Trademark Office*